United States Patent
Suzuki et al.

(10) Patent No.: US 11,786,445 B2
(45) Date of Patent: Oct. 17, 2023

(54) COMPOSITION FOR NATURAL SKIN BRIGHTENING EFFECT

(71) Applicant: L'OREAL, Paris (FR)

(72) Inventors: Jun Suzuki, Kawasaki (JP); Romain Tachon, Tokyo (JP)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/342,226

(22) PCT Filed: Oct. 10, 2017

(86) PCT No.: PCT/JP2017/038093
§ 371 (c)(1),
(2) Date: Apr. 16, 2019

(87) PCT Pub. No.: WO2018/079455
PCT Pub. Date: May 3, 2018

(65) Prior Publication Data
US 2019/0240125 A1 Aug. 8, 2019

(30) Foreign Application Priority Data

Oct. 31, 2016 (JP) ................. 2016-212703

(51) Int. Cl.
A61K 8/19 (2006.01)
A61K 8/02 (2006.01)
A61K 8/25 (2006.01)
A61K 8/26 (2006.01)
A61K 8/29 (2006.01)
A61Q 1/02 (2006.01)

(52) U.S. Cl.
CPC .............. A61K 8/19 (2013.01); A61K 8/0254 (2013.01); A61K 8/0279 (2013.01); A61K 8/25 (2013.01); A61K 8/26 (2013.01); A61K 8/29 (2013.01); A61Q 1/02 (2013.01); A61K 2800/412 (2013.01); A61K 2800/436 (2013.01)

(58) Field of Classification Search
CPC ... A61K 8/26; A61K 8/19; A61K 8/25; A61K 8/29; A61K 8/0254; A61K 8/0279; A61K 2800/412; A61K 2800/436; A61K 2800/26; A61Q 1/02
See application file for complete search history.

(56) References Cited

U.S. PATENT DOCUMENTS

2014/0335136 A1 11/2014 Brieva et al.
2015/0157539 A1* 6/2015 Shimizu .................. A61K 8/25
424/401

FOREIGN PATENT DOCUMENTS

| JP | H09-12430 A | 1/1997 |
|---|---|---|
| JP | H11-152210 A | 6/1999 |
| JP | 2003-519645 A | 6/2003 |
| JP | 2007-145735 A | 6/2007 |
| JP | 2007-197332 A | 8/2007 |
| JP | 2007-533627 A | 11/2007 |
| JP | 2010-513368 A | 4/2010 |
| JP | 2010-538079 A | 12/2010 |
| JP | 2012-167052 A | 9/2012 |
| JP | 2015-083615 A | 4/2015 |
| JP | 2016-124846 A | 7/2016 |
| JP | 2018-108947 A | 7/2018 |
| JP | 2020-015675 A | 1/2020 |
| KR | 10-2005-0016175 A | 2/2005 |
| WO | 2005/039522 A1 | 5/2005 |
| WO | 2008/077728 A2 | 7/2008 |
| WO | 2009/032896 A2 | 3/2009 |
| WO | 2014/012230 A1 | 1/2014 |
| WO | 2016/149917 A1 | 9/2016 |

OTHER PUBLICATIONS

Momentive Marketing Bulletin, "Momentive* Softouch* CC6058 BN powder", revised Apr. 2011 (Year: 2011).*
International Search Report for counterpart Application No. PCT/JP2017/038093, dated Jan. 2, 2018.
Translated Korean Office Action for counterpart Application No. 10-2019-7013827, dated Sep. 11, 2020.
Translation of Decision of Refusal for Japanese Application No. 2016-212703, dated Mar. 29, 2021.
Partial English language translation of Korean Office Action for Application No. 201780065897.8, dated Jun. 21, 2021.
Partial English language translation of Chinese Office Action for Application No. 201780065897.8, dated Jun. 21, 2021.
Machine Translation of Third Party Observation for counterpart Japanese Application No. 2016-212703, dated Oct. 4, 2021.
SOLESPHERE™ H-51 by AGC Chemicals Americas Personal Care & Cosmetics, dated Feb. 16, 2022.
Translated Third Party Opposition for JP Patent No. 6995472, dated Aug. 25, 2022. (Application No. 2016-212703).
English computer generated translation of Cosmetic Ingredient Database: TIMIRONSILK® Blue: Merck, Matsumoto trading, (Date of revision: Apr. 20, 2021).

(Continued)

Primary Examiner — Bethany P Barham
Assistant Examiner — Barbara S Frazier
(74) Attorney, Agent, or Firm — THE MARBURY LAW GROUP, PLLC

(57) ABSTRACT

The present invention relates to a composition for a keratin substance, such as skin, comprising: (a) at least one plate type filler having a particle size of 10 μm or less, preferably 5 μm or less, and more preferably 3 μm or less; (b) at least one pearlescent pigment having a particle size of 15 μm or less, preferably 12 μm or less, and more preferably 10 μm or less; and (c) at least one hollow or porous particle, wherein the (a) plate type filler has a refractive index of 2.0 or less, preferably 1.9 or less, and more preferably 1.8 or less, and the (b) pearlescent pigment has a colored reflection. The composition according to the present invention can provide a keratin substance with sufficient coverage of imperfections on the keratin substance, while providing the keratin substance with brightness and natural finish.

18 Claims, No Drawings

(56) References Cited

OTHER PUBLICATIONS

English computer generated translation of Safety data sheet timiron silk blue, dated Feb. 16, 2022.
Translation of Notice of Reasons for Revocation for counterpart Application No. 2016-212703, dated Nov. 11, 2022.
Matsumoto Trading, "The plate like barium sulfate H series High lubricity barium for makeup products," Apr. 1, 2010, <URL: https://matsumoto-trd.com/product/pdf/concept/k16.pdf>, Machine Translation.
Yamada et al., "research on the optical property of the skin for cosmetics development," and the Transactions of the JSME (in Japanese) (B pieces) 2005, 71 volumes, No. 705, pp. 1436-1444.
Machine translation of Decision on Opposition for counterpart JP Application No. 2016-212703, dated Jun. 23, 2023.

\* cited by examiner

COMPOSITION FOR NATURAL SKIN BRIGHTENING EFFECT

CROSS REFERENCE TO RELATED APPLICATIONS

This is a national stage application of PCT/JP2017/038093, filed internationally on Oct. 10, 2017, which claims priority to Japanese Application No. 2016-212703, filed on Oct. 31, 2016, both of which are incorporated by reference herein in their entireties.

TECHNICAL FIELD

The present invention relates to a composition to be applied onto a keratin substance such as skin, as well as the uses thereof.

BACKGROUND ART

Skin imperfections such as spots, pores and fine lines have been handled with make-up cosmetics. On the other hand, skin imperfections are also becoming a general concern of skincare cosmetic users. In order to hide skin imperfections with skincare cosmetic products as well, a sufficient level of coverage is desired, while not giving an unnatural artificial look.

Conventionally, for hiding skin imperfections with cosmetic products, coloring pigments such as $TiO_2$ and iron oxide are used to cover the skin. However, in this case of using coloring pigments, the skin tends to look dull or unnatural such as to have artificial colored traces. Also, for skincare cosmetic products, such coloring pigments cannot be used or can only be used in a limited amount, since they strongly color the skincare cosmetic products. Furthermore, such coloring pigments generally have a negative impact on the texture of the skincare cosmetic products.

Pearlescent pigments are also used to correct skin imperfections. However, they tend to give a glittering appearance due to their strong reflection property, which is also unnatural. Thus, there is a need for a technology to hide skin imperfections, and naturally brighten up the skin without making the skin look artificial.

DISCLOSURE OF INVENTION

An objective of the present invention is to provide a composition for a keratin substance such as skin which can provide the keratin substance with sufficient coverage of imperfections on the keratin substance, while providing the keratin substance with brightness and natural finish.

The above objective can be achieved by a composition for a keratin substance, such as skin, comprising:
(a) at least one plate type filler having a particle size of 10 µm or less, preferably 5 µm or less, and more preferably 3 µm or less;
(b) at least one pearlescent pigment having a particle size of 15 µm or less, preferably 12 µm or less, and more preferably 10 µm or less; and
(c) at least one hollow or porous particle,
wherein
the (a) plate type filler has a refractive index of 2.0 or less, preferably 1.9 or less, and more preferably 1.8 or less, and the (b) pearlescent pigment has a colored reflection.

The (a) plate type filler may have a particle size of 0.1 µm or more, preferably 0.3 µm or more, and more preferably 0.5 µm or more.

The (a) plate type filler may have a refractive index of 1.2 or more, preferably 1.4 or more, and more preferably 1.6 or more.

The (a) plate type filler may comprise at least one inorganic material selected from the group consisting of boron nitride, barium sulfate, bismuth oxychloride, alumina, and composite powders based on titanium oxide and a substrate comprising talc, mica, barium sulfate, boron nitride, bismuth oxychloride, alumina, or mixtures thereof.

The (a) plate type filler may consist essentially of boron nitride.

The amount of the (a) plate type filler may range from 0.001% to 10% by weight, preferably from 0.01% to 5% by weight, and more preferably from 0.1% to 3% by weight, relative to the total weight of the composition.

The (b) pearlescent pigment may have a blue reflection.

The (b) pearlescent pigment may have a particle size of 1 µm or more, preferably 3 µm or more, and more preferably 5 µm or more.

The (b) pearlescent pigment may comprise mica and metal oxide, preferably titanium oxide and/or tin oxide.

The amount of the (b) pearlescent pigment may range from 0.001% to 10% by weight, preferably from 0.01% to 5% by weight, and more preferably from 0.1% to 3% by weight, relative to the total weight of the composition.

The (c) hollow or porous particle may have a particle size of 15 µm or less, preferably 12 µm or less, and more preferably 10 µm or less.

The (c) hollow or porous particle may comprise at least one inorganic material selected from the group consisting of mica, synthetic mica, talc, sericite, boron nitride, glass, calcium carbonate, barium sulfate, titanium oxide, hydroxyapatite, silica, silicate, calcium sodium borosilicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

The amount of the (c) hollow or porous particle may range from 0.001% to 10% by weight, preferably from 0.01% to 5% by weight, and more preferably from 0.1% to 3% by weight, relative to the total weight of the composition.

The present invention also relates to a cosmetic process for a keratin substance such as skin, comprising the step of applying the composition according to the present invention.

The present invention also relates to a use of a combination of
(a) at least one plate type filler having a particle size of 10 µm or less, preferably 5 µm or less, and more preferably 3 µm or less;
(b) at least one pearlescent pigment having a particle size of 15 µm or less, preferably 12 µm or less, and more preferably 10 µm or less; and
(c) at least one hollow or porous particle,
wherein
the (a) plate type filler has a refractive index of 2.0 or less, preferably 1.9 or less, and more preferably 1.8 or less, and
the (b) pearlescent pigment has a colored reflection,
on a keratin substance,
for sufficiently covering imperfections on the keratin substance, while providing the keratin substance with brightness and natural finish.

BEST MODE FOR CARRYING OUT THE INVENTION

After diligent research, the inventors have discovered that it is possible to provide a composition for a keratin substance such as skin which can provide the keratin substance with sufficient coverage of imperfections on the keratin substance, while providing the keratin substance with brightness and natural finish.

Thus, the present invention mainly relates to a composition for a keratin substance, such as skin, comprising:
(a) at least one plate type filler having a particle size of 10 μm or less, preferably 5 μm or less, and more preferably 3 μm or less;
(b) at least one pearlescent pigment having a particle size of 15 μm or less, preferably 12 μm or less, and more preferably 10 μm or less; and
(c) at least one hollow or porous particle,
wherein
the (a) plate type filler has a refractive index of 2.0 or less, preferably 1.9 or less, and more preferably 1.8 or less, and
the (b) pearlescent pigment has a colored reflection.

The above composition according to the present invention can sufficiently cover imperfections, such as spots, pores, and fine lines, on a keratin substance, and provide the keratin substance with sufficient brightness and natural appearance after the application of the composition onto the keratin substance.

In particular, the above composition according to the present invention can decrease the visibility of skin color defects such as spots and/or microreliefs on skin such as pores and fine lines, providing skin with brightness, without providing skin with a glittering appearance and unnatural finish.

For example, the composition according to the present invention does not leave color (e.g., white) traces on a keratin substance such as skin, which may cause an unnatural finish.

The composition according to the present invention may not be strongly colored, because no use of coloring pigment is necessary. Accordingly, the composition according to the present invention is preferable for skincare cosmetic products. On the other hand, it is not preferable that the composition according to the present invention be used as a skin makeup cosmetic product. Thus, in one embodiment, the composition according to the present invention may be a skincare cosmetic composition, and may not be a skin makeup cosmetic composition.

Hereafter, the present invention will be described in a detailed manner.

[Composition]

One aspect of the present invention relates to a composition for a keratin substance, such as skin, comprising:
(a) at least one plate type filler having a particle size of 10 μm or less, preferably 5 μm or less, and more preferably 3 μm or less;
(b) at least one pearlescent pigment having a particle size of 15 μm or less, preferably 12 μm or less, and more preferably 10 μm or less; and
(c) at least one hollow or porous particle,
wherein
the (a) plate type filler has a refractive index of 2.0 or less, preferably 1.9 or less, and more preferably 1.8 or less, and
the (b) pearlescent pigment has a colored reflection.

(Plate Type Filler)

The composition according to the present invention comprises at least one (a) plate type filler with a limited particle size and a limited refractive index. A single type of the (a) plate type filler may be used, or two or more different types of the (a) plate type fillers may be used in combination.

The (a) plate type filler has a particle size of 10 μm or less, preferably 5 μm or less, and more preferably 3 μm or less, and a refractive index of 2.0 or less, preferably 1.9 or less, and more preferably 1.8 or less.

The aspect ratio of the (a) plate type filler may be at least 5, preferably more than 10, more preferably more than 20, and even more preferably more than 50. The aspect ratio can be determined by the average thickness and the average length according to the formula: aspect ratio=length/thickness.

Thus, the (a) plate type filler may have a length of 10 μm or less, preferably 5 μm or less, and more preferably 3 μm or less.

The (a) plate type filler can contribute to naturally brightening a keratin substance such as skin by providing an appropriate coverage level due to its characteristic refractive index. It should be noted that the use of conventional white pigments such as $TiO_2$ with a refractive index of more than 2.0 can provide a brightness which is too strong and that may cause an unnatural appearance. It should also be noted that the use of conventional plate type fillers with a particle size of more than 10 μm cannot sufficiently cover a keratin substance, and cannot provide sufficient brightness.

The particle size is expressed as the mean volume diameter (D[0.5]).

It may be preferable that the (a) plate type filler have a particle size of 0.1 μm or more, preferably 0.3 μm or more, and more preferably 0.5 μm or more. Thus, it may be preferable that the (a) plate type filler have a length of 0.1 μm or more, preferably 0.3 μm or more, and more preferably 0.5 μm or more.

It may also be preferable that the (a) plate type filler have a refractive index of 1.2 or more, preferably 1.4 or more, and more preferably 1.6 or more.

It is preferable that the (a) plate type filler comprise at least one inorganic particle.

It is more preferable that the (a) plate type filler comprise at least one inorganic material selected from the group consisting of boron nitride, barium sulfate, bismuth oxychloride, alumina, and composite powders based on titanium oxide and a substrate comprising talc, mica, barium sulfate, boron nitride, bismuth oxychloride, alumina, or mixtures thereof.

It is even more preferable that the (a) plate type filler consist essentially of boron nitride. It is most preferable that the (a) plate type filler consist only of boron nitride.

As examples of commercial products of boron nitride, mention may be made of the following products: PUHP3002 and PUHP 3008 from Saint Gobains Ceramics (mean particle size 2 μm and 8 μm, respectively), the PUHP1030L from Saint Gobain Ceramics (mean particle size 3 μm), the Y-20040 powder from Momentive Performance Materials, the RONAFLAIR BORONEIGE SF-3 from MERCK, or mixtures thereof.

The amount of the (a) plate type filler may range from 0.001% to 10% by weight, preferably from 0.01% to 5% by weight, and more preferably from 0.1% to 3% by weight, relative to the total weight of the composition.

(Pearlescent Pigment)

The composition according to the present invention comprises at least one (b) pearlescent pigment with a limited particle size and a colored reflection. A single type of the (b) pearlescent pigment may be used, or two or more different types of the (b) pearlescent pigments may be used in combination.

The (b) pearlescent pigment has a particle size of 15 μm or less, preferably 12 μm or less, and more preferably 10 μm or less; and has a colored reflection.

The (b) pearlescent pigment with a limited particle size and a colored reflection can contribute to color correction of a keratin substance such as skin by mixing the colored reflection with the original color of the keratin substance, and to natural appearance. It should be noted that the use of conventional pearlescent pigments with a particle size of more than 15 μm cannot sufficiently cover the keratin substance, and cannot provide sufficient brightness but provides a glittering appearance and unnatural finish.

The particle size is expressed as the mean volume diameter (D[0.5]).

It may be preferable that the (b) pearlescent pigment have a particle size of 1 μm or more, preferably 3 μm or more, and more preferably 5 μm or more.

The (b) pearlescent pigment can be in any shape. For example, it is possible to use a pearlescent pigment in the form of a plate with an aspect ratio of at least 5, preferably more than 10, more preferably more than 20, and even more preferably more than 50. The aspect ratio can be determined by the average thickness and the average length according to the formula: aspect ratio=length/thickness.

If a plate-like particle is used for the (b) pearlescent pigment, it is preferable that the plate-like particle have a length of 15 μm or less, preferably 12 μm or less, and more preferably 10 μm or less.

The term "pearlescent pigments", which may also be called "nacres", should be understood as meaning colored particles of any form, which may or may not be iridescent, especially produced by certain molluscs in their shell, or alternatively synthesized, and which have a color effect via optical interference.

Examples of the (b) pearlescent pigment that may be mentioned include nacres such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

It may be preferable that the (b) pearlescent pigment comprise mica and metal oxide, preferably titanium oxide and/or tin oxide.

The (b) pearlescent pigment may have a reflection with a color such as white, blue, yellow, pink, red, bronze, orange, brown, gold and copper.

It may be preferable that the (b) pearlescent pigment can show a white color. For example, the (b) pearlescent pigment can show a white color on a white background.

It may also be preferable that the (b) pearlescent pigment have a blue reflection. For example, the (b) pearlescent pigment can show a blue reflection on a black background. Here, the term "blue" means visible light with a wavelength of from about 450 to about 495 nm.

The (b) pearlescent pigment with a blue reflection can contribute anti-yellowness. Therefore, it can be advantageous in covering color imperfections on a keratin substance, such as spots on skin.

As illustrations of the (b) pearlescent pigment that may be introduced into the composition according to the present invention, mention may be made of Ronaflair Balance Red/Blue/Gold/Green, and Timiron Silk Blue/Green/Red/Gold sold by the company Merck, Sunshine Soft Fine Gold/Red/violet/Blue/Green sold by the company Sun Chemical, Helios R10Y/R/B/G sold by the company Topy, and Flammenco Summit Aqua series sold by the company BASF.

Still, as examples of the (b) pearlescent pigment, mention may also be made of particles comprising a borosilicate substrate coated with titanium oxide.

The amount of the (b) pearlescent pigment may range from 0.001% to 10% by weight, preferably from 0.01% to 5% by weight, and more preferably from 0.1% to 3% by weight, relative to the total weight of the composition.

(Hollow or Porous Particle)

The composition according to the present invention comprises at least one (c) hollow or porous particle. A single type of the (c) hollow or porous particle may be used, or two or more different types of the (c) hollow or porous particles may be used in combination.

The (c) hollow or porous particle may be either a hollow particle or a porous particle. On the other hand, it is also possible to use a particle which is hollow and porous as the (c) hollow or porous particle.

The (c) hollow or porous particle can contribute to making the color of a keratin substance uniform, and make imperfections on a keratin substance less visible by its blurring effects. Thus, the (c) hollow or porous particle can enhance coverage of a keratin substance and provide sufficient brightness.

The particle size is expressed as the mean volume diameter (D[0.5]).

It may be preferable that the (c) hollow or porous particle have a particle size of 15 μm or less, preferably 12 μm or less, and more preferably 10 μm or less.

The (c) hollow or porous particle can be in any shape. For example, it is possible to use a hollow or porous particle in the form of a plate with an aspect ratio of at least 5, preferably more than 10, more preferably more than 20, and even more preferably more than 50. The aspect ratio can be determined by the average thickness and the average length according to the formula: aspect ratio=length/thickness.

If a plate-like particle is used for the (c) hollow or porous particle, it is preferable that the plate-like particle have a length ranging from more than 100 nm to 15 μm or less, preferably 12 μm or less, and more preferably 10 μm or less.

In a preferred embodiment, the (c) hollow or porous particle has a spherical shape.

The material of the (c) hollow or porous particle is not limited. The material of the (c) hollow or porous particle may be selected from at least one organic material and at least one inorganic material.

It is preferable that the organic material be selected from organic polymers.

The organic polymer may be selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, wax, amidosulfonic acid polyvalent metal salts, acylated amino acids, and mixtures thereof.

As fluoropolymers, for example, PTFE may be used. As amidosulfonic acid polyvalent metal salts, for example, N-lauroyltaurine calcium may be used. As acylated amino acids, lauroyllysine may be used. Polyamides such as Nylon®, polyhydroxyalkanoates such as polylactic acids, poly(meth)acrylates such as polymethylmethacrylates, silicones, and mixtures thereof are more preferable.

In particular, as the organic polymer, copolystyrene is preferable, and styrene/acrylate copolymer, and cross-linked styrene/methyl methacrylate copolymer are more preferable. Thus, as the small hollow core particles, for example, Sunspheres (small hollow particles made from styrene/ acrylate copolymer) marketed by Rohm and Haas, as well as SX859(A) and SX866(B) (small hollow particles made form cross-linked styrene/methyl methacrylate copolymer) marketed by JSR Corp. in Japan, are preferable.

It is preferable that the (c) hollow or porous particle comprise at least one inorganic material.

It may be preferable that the (c) hollow or porous particle comprise at least one inorganic material selected from the group consisting of mica, synthetic mica, talc, sericite, boron nitride, glass, calcium carbonate, barium sulfate, titanium oxide, hydroxyapatite, silica, silicate, calcium sodium borosilicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof.

In particular, silica and calcium sodium borosilicate are more preferable.

The organic and/or inorganic material can be porous. The porosity of the material may be characterized by a specific surface area of from 0.05 $m^2/g$ to 1,500 $m^2/g$, preferably from 0.1 $m^2/g$ to 1,000 $m^2/g$, and more preferably from 0.2 $m^2/g$ to 500 $m^2/g$ according to the BET method.

In a particular embodiment, the (c) hollow or porous particle may have at least one coating. The material of the coating is not limited, but an organic material such as an amino acid, an N-acylamino acid, an amido, a silicone and a modified silicone, may be preferable. As the organic material, mention may be made of lauroyl lysine and acryl-modified silicone.

As examples of the (c) hollow or porous particle, mention may be made of Luxsil Cosmetics Microspheres sold by the company Potters Industries, Sunspheres H-51, H-53, H-31, and H-33 sold by the company AGC Si-Tech, Sunspheres Powder sold by the company Dow Chemical, Covabead LH85 sold by the company Sensient, and Dow Corning VM-2270 Aerogel Fine particles sold by the company Dow Corning).

The amount of the (c) hollow or porous particle may range from 0.001% to 10% by weight, preferably from 0.01% to 5% by weight, and more preferably from 0.1% to 3% by weight, relative to the total weight of the composition.

(Oil)

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils, and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:
(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

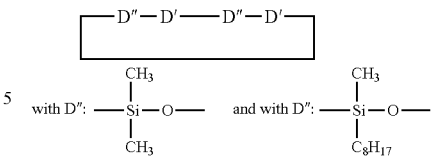

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 mm$^2$/s; and
the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

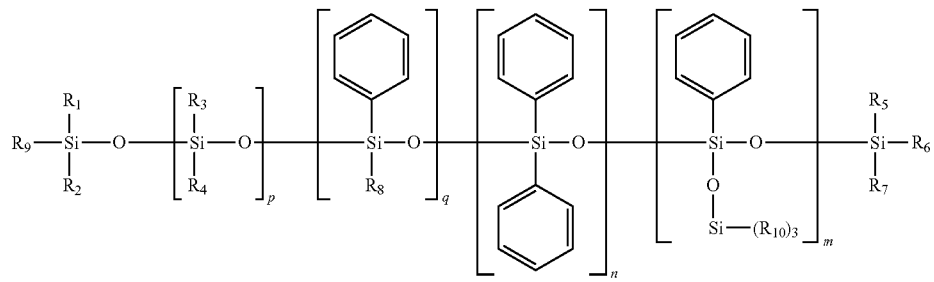

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and
linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It is preferable that the oil be chosen from hydrocarbon oils, ester oils, silicone oils, and mixtures thereof.

The amount of the oil in the composition according to the present invention may range from 0.1% to 40% by weight, preferably from 1% to 35% by weight, more preferably from 2% to 30% by weight, even more preferably from 5 to 25% by weight, and even further more preferably from 10 to 20% by weight, relative to the total weight of the composition.

(Surfactant)

The composition according to the present invention comprises at least one surfactant. A single type of surfactant may be used, or two or more different types of surfactants may be used in combination.

The surfactant used in the present invention may be selected from the group consisting of anionic surfactants, amphoteric surfactants, cationic surfactants and nonionic surfactants, preferably nonionic surfactants.

The amount of the surfactant(s) may be 15% by weight or less, preferably 10% by weight or less, and more preferably 5% by weight or less, relative to the total weight of the composition according to the present invention, with the proviso that the amount of the surfactant(s) is not zero. The amount of the surfactant (s) may be 0.1% by weight or more, preferably 0.5% by weight or more, and more preferably from 1.0% by weight or more, relative to the total weight of the composition.

The amount of the surfactant(s) in the composition according to the present invention may range from 0.1% to 15% by weight, preferably from 0.5% to 10% by weight, and more preferably from 1% to 5% by weight, relative to the total weight of the composition.

(1) Anionic Surfactants

The composition according to the present invention may comprise at least one anionic surfactant. Two or more anionic surfactants may be used in combination.

It is preferable that the anionic surfactant be selected from the group consisting of ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates; ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$) acyl isethionates; N—($C_6$-$C_{24}$)acyl taurates; $C_6$-$C_{30}$ fatty acid salts; coconut oil acid salts or hydrogenated coconut oil acid salts; ($C_8$-$C_{20}$)acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$) alkylaryl ether carboxylic acid salts; and polyoxyalkylenated ($C_6$-$C_{30}$)alkylamido ether carboxylic acid salts; and corresponding acid forms.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It is more preferable that the anionic surfactant be selected from salts of ($C_6$-$C_{30}$)alkyl sulfate, ($C_6$-$C_{30}$)alkyl ether sulfates or polyoxyalkylenated ($C_6$-$C_{30}$)alkyl ether carboxylic acid salified or not.

(2) Amphoteric Surfactants

The composition according to the present invention may comprise at least one amphoteric surfactant. Two or more amphoteric surfactants may be used in combination.

The amphoteric or zwitterionic surfactants can be, for example (non-limiting list), amine derivatives such as aliphatic secondary or tertiary amine, and optionally quaternized amine derivatives, in which the aliphatic radical is a linear or branched chain including 8 to 22 carbon atoms and containing at least one water-solubilizing anionic group (for example, carboxylate, sulphonate, sulphate, phosphate or phosphonate).

The amphoteric surfactant may preferably be selected from the group consisting of betaines and amidoaminecarboxylated derivatives.

It is preferable that the amphoteric surfactant be selected from betaine-type surfactants.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA International Cosmetic Ingredient Dictionary & Handbook, 15th Edition, 2014, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

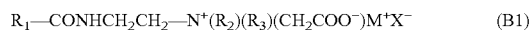

in which:

$R_1$ denotes an alkyl radical of an acid $R_1$—COOH present in hydrolysed coconut oil, a heptyl, nonyl or undecyl radical, $R_2$ denotes a beta-hydroxyethyl group, $R_3$ denotes a carboxymethyl group, $M^+$ denotes a cationic ion derived from alkaline metals such as sodium; ammonium ion; or an ion derived from an organic amine;

$X^-$ denotes an organic or inorganic anionic ion such as halides, acetates, phosphates, nitrates, alkyl($C_1$-$C_4$)sulfates, alkyl($C_1$-$C_4$)— or alkyl($C_1$-$C_4$)aryl-sulfonates, particularly methylsulfate and ethylsulfate; or $M^+$ and $X^-$ are not present;

in which:

$R_1'$ denotes an alkyl radical of an acid $R_1'$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso-form, or an unsaturated $C_{17}$ radical, B represents —$CH_2CH_2OX'$, C represents —$(CH_2)_z$—Y', with z=1 or 2, X' denotes a —$CH_2$—COOH group, —$CH_2$—COOZ', —$CH_2CH_2$—COOH, —$CH_2CH_2$—COOZ' or a hydrogen atom, and Y' denotes —COOH, —COOZ', —$CH_2$—CHOH—$SO_3Z'$, —$CH_2$—CHOH—$SO_3H$ radical or a —$CH_2$—CH(OH)—$SO_3$—Z' radical, wherein Z' represents an ion of an alkaline or alkaline earth metal such as sodium, an ion derived from an organic amine or an ammonium ion;

and

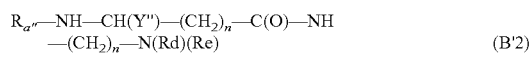

in which:

Y" denotes —C(O)OH, —C(O)OZ", —$CH_2$—CH(OH)—$SO_3H$ or —$CH_2$—CH(OH)—$SO_3$—Z", wherein Z" denotes a cationic ion derived from alkaline metal or alkaline-earth metals such as sodium, an ion derived from organic amine or an ammonium ion;

Rd and Re denote a $C_1$-$C_4$ alkyl or $C_1$-$C_4$ hydroxyalkyl radical;

$R_{a''}$ denotes a $C_{10}$-$C_{30}$ group alkyl or alkenyl group from an acid, and n and n' independently denote an integer from 1 to 3.

It is preferable that the amphoteric surfactant with formula B1 and B2 be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Among compounds of formula (B'2) mention may be made of sodium diethylaminopropyl cocoaspartamide (CTFA) marketed by CHIMEX under the denomination CHIMEXANE HB.

(3) Cationic Surfactants

The composition according to the present invention may comprise at least one cationic surfactant. Two or more cationic surfactants may be used in combination.

The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:
those of general formula (B3) below:

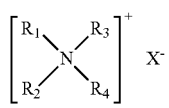

(B3)

wherein
$R_1$, $R_2$, $R_3$, and $R_4$, which may be identical or different, are chosen from linear and branched aliphatic radicals including from 1 to 30 carbon atoms and optionally including heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and $X^-$ is chosen from halides, phosphates, acetates, lactates, ($C_2$-$C_6$) alkyl sulfates and alkyl- or alkylarylsulfonates; quaternary ammonium salts of imidazoline, for instance those of formula (B4) below:

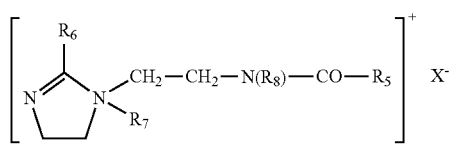

(B4)

wherein:
$R_5$ is chosen from alkenyl and alkyl radicals including from 8 to 30 carbon atoms, for example fatty acid derivatives of tallow or of coconut;
$R_6$ is chosen from hydrogen, $C_1$-$C_4$ alkyl radicals, and alkenyl and alkyl radicals including from 8 to 30 carbon atoms;
$R_7$ is chosen from $C_1$-$C_4$ alkyl radicals;
$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals including from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

Di or tri quaternary ammonium salts of formula (B5):

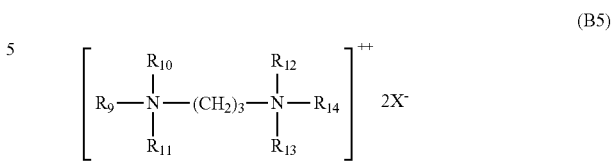

(B5)

wherein:
$R_9$ is chosen from aliphatic radicals including from 16 to 30 carbon atoms;
$R_{10}$ is chosen from hydrogen or alkyl radicals including from 1 to 4 carbon atoms or a group —$(CH_2)_3(R_{16a})(R_{17a})(R_{18a})N^+X^-$;
$R_{11}$, $R_{12}$, $R_{13}$, $R_{14}$, $R_{16a}$, $R_{17a}$, and $R_{18a}$, which may be identical or different, are chosen from hydrogen and alkyl radicals including from 1 to 4 carbon atoms; and
$X^-$ is chosen from halides, acetates, phosphates, nitrates, ethyl sulfates, and methyl sulfates.

An example of one such diquaternary ammonium salt is FINQUAT CTP of FINETEX (Quaternium-89) or FINQUAT CT (Quaternium-75);
and
quaternary ammonium salts including at least one ester function, such as those of formula (B6) below:

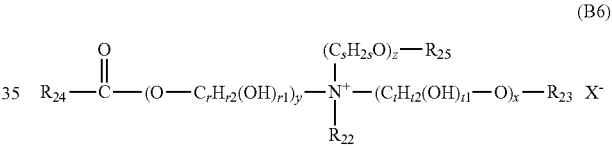

(B6)

wherein:
$R_{22}$ is chosen from $C_1$-$C_6$ alkyl radicals and $C_1$-$C_6$ hydroxyalkyl and dihydroxyalkyl radicals; $R_{23}$ is chosen from:
the radical below:

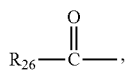

linear and branched, saturated and unsaturated $C_1$-$C_{22}$ hydrocarbon-based radicals $R_{27}$, and hydrogen,
$R_{25}$ is chosen from:
the radical below:

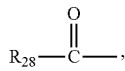

linear and branched, saturated and unsaturated $C_1$-$C_6$ hydrocarbon-based radicals $R_{29}$, and hydrogen,
$R_{24}$, $R_{26}$, and $R_{28}$, which may be identical or different, are chosen from linear and branched, saturated and unsaturated, $C_7$-$C_{21}$, hydrocarbon-based radicals;
r, s, and t, which may be identical or different, are chosen from integers ranging from 2 to 6;

each of r1 and t1, which may be identical or different, is 0 or 1, and r2+r1=2r and t1+2t=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and include from 12 to 22 carbon atoms, or short and include from 1 to 3 carbon atoms. When $R_{25}$ is a hydrocarbon-based radical $R_{29}$, it may include, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium including an ester function, are other non-limiting examples of anions that may be used according to the present invention. In one embodiment, the anion $X^-$ is chosen from chloride and methyl sulfate.

In another embodiment, the ammonium salts of formula (B6) may be used, wherein:

$R_{22}$ is chosen from methyl and ethyl radicals, x and y are equal to 1;

z is equal to 0 or 1;

r, s and t are equal to 2;

$R_{23}$ is chosen from:

the radical below:

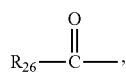

methyl, ethyl, and $C_{14}$-$C_{22}$ hydrocarbon-based radicals, hydrogen;

$R_{25}$ is chosen from:

the radical below:

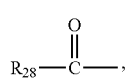

and hydrogen;

$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (B6) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may include from 14 to 18 carbon atoms, and may be derived, for example, from a plant oil, for instance palm oil and sunflower oil. When the compound includes several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the composition according to the present invention include the ammonium salts including at least one ester function described in U.S. Pat. Nos. 4,874,554 and 4,137,180.

The quaternary ammonium salts mentioned above that may be used in the composition according to the present invention include, but are not limited to, those corresponding to formula (I), for example tetraalkylammonium chlorides, for instance dialkyldimethylammonium and alkyltrimethylammonium chlorides in which the alkyl radical includes from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the composition according to the present invention is chosen from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(4) Nonionic Surfactants

The composition according to the present invention may comprise at least one nonionic surfactant. Two or more nonionic surfactants may be used in combination.

The nonionic surfactants are compounds well known in and of themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:
monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols,
saturated or unsaturated, linear or branched, monooxyalkylenated or polyoxyalkylenated $C_8$-$C_{30}$ amides,
esters of saturated or unsaturated, linear or branched, $C_8$-$C_{30}$ acids and of polyalkylene glycols,
monooxyalkylenated or polyoxyalkylenated esters of saturated or unsaturated, linear or branched, $C_8$-$C_{30}$ acids and of sorbitol,
saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated saturated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 50 oxyethylene units (Ceteareth-10 to Ceteareth-50, as the CTFA names); the adducts of ethylene oxide with cetyl alcohol, especially those containing from 10 to 50 oxyethylene units (Ceteth-10 to Ceteth-50, as the CTFA names); the adducts of ethylene oxide with stearyl alcohol, especially those containing from 10 to 50 oxyethylene units (Steareth-10 to Steareth-50, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

Examples of polyoxyethylenated unsaturated fatty alcohol (or $C_8$-$C_{30}$ alcohols) that may be mentioned include the adducts of ethylene oxide with oleyl alcohol, especially those containing from 2 to 50 oxyethylene units and more particularly those containing from 10 to 40 oxyethylene units (Oleth-10 to Oleth-40, as the CTFA names); and mixture thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

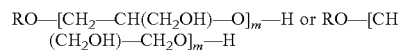

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

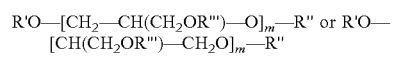

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate), glyceryl laurate or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or a branched $C_{12}$-$C_{22}$ acyl chain such as an oleyl or isostearyl group. More preferably, the nonionic surfactant according to the present invention is PEG-20 glyceryl triisostearate.

According to one of the embodiments of the present invention, the nonionic surfactant may be selected from copolymers of ethylene oxide and of propylene oxide, in particular copolymers of the following formula:

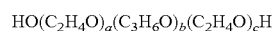

in which a, b and c are integers such that a+c ranges from 2 to 100 and b ranges from 14 to 60, and mixtures thereof.

According to one of the embodiments of the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

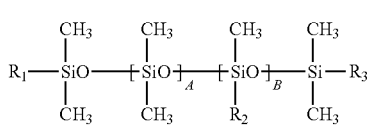

in which:
R$_1$, R$_2$ and R$_3$, independently of each other, represent a C$_1$-C$_6$ alkyl radical or a radical —(CH$_2$)$_x$—(OCH$_2$CH$_2$)$_y$—(OCH$_2$CH$_2$)$_z$—OR$_4$, at least one radical R$_1$, R$_2$ or R$_3$ not being an alkyl radical; R$_4$ being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

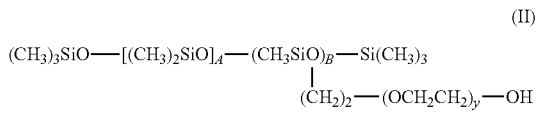

in which A is an integer ranging from 20 to 105, B is an integer ranging from 2 to 10 and y is an integer ranging from 10 to 20.

As examples of silicone surfactants of formula (I), mention may also be made of the compounds of formula (III):

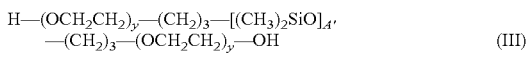

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

(Optional Ingredients)

The composition according to the present invention may also comprise various adjuvants conventionally used in compositions for a keratin substance such as skin, scalp and lips, which may be selected from cosmetic active ingredients such as whitening agents, anionic, non-ionic, cationic, amphoteric or zwitterionic polymers, or mixtures thereof, antioxidants, thickening agents, sequestering agents, fragrances, dispersing agents, conditioning agents, film-forming agents, ceramides, preservatives and opacifying agents.

The composition according to the present invention may comprise water.

The amount of water in the composition according to the present invention may range from 50% to 99% by weight, preferably from 60% to 95% by weight, and more preferably from 70 to 90% by weight, relative to the total weight of the composition.

The composition according to the present invention may further comprise at least one organic solvent which is miscible with water at ambient temperature (25° C.).

As examples of the organic solvent which is miscible with water at ambient temperature (25° C.), mention may be made of, for example,
monoalcohols having 2 to 6 carbon atoms, such as ethanol and isopropanol;
polyols having 2 to 20 carbon atoms, preferably having 2 to 10 carbon atoms, and more preferably having 2 to 6 carbon atoms, such as glycerin, as well as alkylene glycols such as propylene glycol, butylene glycol, pentylene glycol, hexylene glycol, dipropylene glycol, and diethylene glycol;
glycol ethers (in particular, having 3 to 16 carbon atoms) (such as (C$_1$-C$_4$) alkyl ethers of mono-, di-, or tripropylene glycol, and (C$_1$-C$_4$) alkyl ethers of mono-, di-, or triethylene glycol); and
mixtures thereof.

The composition according to the present invention may comprise the aforementioned water-miscible organic solvent(s) in an amount ranging from 0.1 to 30% by weight, preferably ranging from 5 to 25% by weight, and more preferably ranging from 10 to 20% by weight, with respect to the total weight of the composition. In particular, it is preferable that ethanol be contained in an amount of 0.1 to 15% by weight, more preferably 1 to 10% by weight, if ethanol is present in the composition. It is also preferable that alkylene glycol(s) be contained in an amount of 0.1 to 25% by weight, if alkylene glycol(s) is/are present in the composition, with respect to the total weight of the composition.

The form of the composition according to the present invention is not particularly limited, and may take various forms such as an emulsion (O/W or W/O form), an aqueous gel, an aqueous solution, or the like. It is preferable that the composition according to the present invention be in the form of a water-based solution.

The composition according to the present invention can be a cosmetic composition, preferably a cosmetic composition for a keratin substance such as skin, scalp, lips, and the like. In one embodiment, the composition according to the present invention is not a makeup cosmetic composition, while the composition according to the present invention may be used for forming a makeup base on a keratin substance. In another embodiment, the composition according to the present invention is a cosmetic composition for caring for a keratin substance, preferably a skincare cosmetic composition such as a cosmetic water, a serum, a lotion, and a milk.

[Preparation]

The composition according to the present invention can be prepared by mixing the ingredients (a) to (c), as essential ingredients, and optional ingredient(s), if necessary, as explained above.

The method and means to mix the above essential and optional ingredients are not limited. Any conventional method and means can be used to mix the above essential and optional ingredients to prepare the first or second composition.

The present invention may relate to a process for preparing a composition for a keratin substance such as skin, comprising the step of mixing:

(a) at least one plate type filler having a particle size of 10 µm or less, preferably 5 µm or less, and more preferably 3 µm or less;

(b) at least one pearlescent pigment having a particle size of 15 µm or less, preferably 12 µm or less, and more preferably 10 µm or less; and (c) at least one hollow or porous particle, wherein the (a) plate type filler has a refractive index of 2.0 or less, preferably 1.9 or less, and more preferably 1.8 or less, and the (b) pearlescent pigment has a colored reflection in a physiologically acceptable carrier which may include, for example, water, alcohol or polyol.

The present invention may also relate to a process for preparing a composition for a keratin substance such as skin, comprising the step of combining:

(a) at least one plate type filler having a particle size of 10 µm or less, preferably 5 or less, and more preferably 3 µm or less;

(b) at least one pearlescent pigment having a particle size of 15 µm or less, preferably 12 µm or less, and more preferably 10 µm or less; and (c) at least one hollow or porous particle, wherein the (a) plate type filler has a refractive index of 2.0 or less, preferably 1.9 or less, and more preferably 1.8 or less, and the (b) pearlescent pigment has a colored reflection, in the composition, for making the cosmetic composition sufficiently cover imperfections on the keratin substance, while providing the keratin substance with brightness and natural finish.

[Cosmetic Process]

The present invention also relates to a cosmetic process for a keratin substance such as skin, comprising the steps of applying the composition according to the present invention as explained above.

It may be preferable that the cosmetic process according to the present invention comprise a step of washing a keratin substance before the step of applying the composition according to the present invention onto the keratin substance.

The step of applying the composition according to the present invention onto a keratin substance such as skin can be performed by a conventional means such as a puff, or even by the hands.

The keratin substance to which the composition according to the present invention has been applied can be left for an appropriate time which is required to treat the keratin substance. The time length for the treatment is not limited, but it may be from 1 minute to 1 hour, preferably 1 minute to 30 minutes, and more preferably 1 minute to 15 minutes. For example, the time for dyeing the keratin substance may be from 1 to 20 minutes, preferably 5 to 15 minutes.

The keratin substance may be treated at room temperature. Alternatively, the keratin substance can be treated with the composition according to the present invention at a temperature of from 10° C. to 45° C., preferably from 15° C. to 40° C., more preferably from 20° C. to 35° C., and even more preferably from 25° C. to 35° C.

[Use]

The present invention also relates to a use of a combination of (a) at least one plate type filler having a particle size of 10 µm or less, preferably 5 µm or less, and more preferably 3 µm or less;

(b) at least one pearlescent pigment having a particle size of 15 µm or less, preferably 12 µm or less, and more preferably 10 µm or less; and (c) at least one hollow or porous particle, wherein the (a) plate type filler has a refractive index of 2.0 or less, preferably 1.9 or less, and more preferably 1.8 or less, and the (b) pearlescent pigment has a colored reflection, on a keratin substance, for sufficiently covering imperfections on the keratin substance, while providing the keratin substance with brightness and natural finish.

It is preferable that the above use be performed on keratin substance in order for sufficiently cover skin imperfections, while providing the skin with brightness and natural finish.

The present invention may also relate to a use of a combination of (a) at least one plate type filler having a particle size of 10 µm or less, preferably 5 µm or less, and more preferably 3 µm or less;

(b) at least one pearlescent pigment having a particle size of 15 µm or less, preferably 12 µm or less, and more preferably 10 µm or less; and (c) at least one hollow or porous particle, wherein the (a) plate type filler has a refractive index of 2.0 or less, preferably 1.9 or less, and more preferably 1.8 or less, and the (b) pearlescent pigment has a colored reflection, in a cosmetic composition, for making the cosmetic composition sufficiently cover imperfections on the keratin substance, while providing the keratin substance with brightness and natural finish.

EXAMPLES

The present invention will be described in a more detailed manner by way of examples. However, these examples should not be construed as limiting the scope of the present invention.

Examples 1-2 and Comparative Examples 1-6

[Preparation]

Each of the compositions according to Examples 1-2 (Ex. 1 to Ex. 2) and Comparative Examples 1-6 (Comp. Ex. 1 to Comp. Ex. 6) was prepared by mixing the ingredients shown in Table 1. The numerical values for the amounts of the ingredients are all based on "% by weight" as active raw materials.

TABLE 1

|  | Ex. 1 | Ex. 2 | Comp. Ex. 1 | Comp. Ex. 2 | Comp. Ex. 3 | Comp. Ex. 4 | Comp. Ex. 5 | Comp Ex. 6 |
|---|---|---|---|---|---|---|---|---|
| Glyceryl Stearate (and) PEG-100 Stearate | 1.60 | 1.60 | 1.60 | 1.60 | 1.60 | 1.60 | 1.60 | 1.60 |
| Polysorbate 60 | 0.70 | 0.70 | 0.70 | 0.70 | 0.70 | 0.70 | 0.70 | 0.70 |
| Cetyl Alcohol | 1.00 | 1.00 | 1.00 | 1.00 | 1.00 | 1.00 | 1.00 | 1.00 |
| Stearic Acid | 0.50 | 0.50 | 0.50 | 0.50 | 0.50 | 0.50 | 0.50 | 0.50 |
| Hydrogenated Polyisobutene | 1.00 | 1.00 | 1.00 | 1.00 | 1.00 | 1.00 | 1.00 | 1.00 |
| Octyldodecanol | 1.00 | 1.00 | 1.00 | 1.00 | 1.00 | 1.00 | 1.00 | 1.00 |
| Cyclohexasiloxane | 11.00 | 11.00 | 11.00 | 11.00 | 11.00 | 11.00 | 11.00 | 11.00 |
| Water | qsp 100 | qsp 100 | qsp 100 | qsp 100 | qsp 100 | qsp 100 | qsp 100 | qsp 100 |
| Glycerin | 5.00 | 5.00 | 5.00 | 5.00 | 5.00 | 5.00 | 5.00 | 5.00 |
| Disodium EDTA | 0.20 | 0.20 | 0.20 | 0.20 | 0.20 | 0.20 | 0.20 | 0.20 |
| Caprylyl Glycol | 0.20 | 0.20 | 0.20 | 0.20 | 0.20 | 0.20 | 0.20 | 0.20 |
| Dipropylene Glycol | 15.00 | 15.00 | 15.00 | 15.00 | 15.00 | 15.00 | 15.00 | 15.00 |
| Phenoxyethanol | 0.40 | 0.40 | 0.40 | 0.40 | 0.40 | 0.40 | 0.40 | 0.40 |
| Xanthan Gum | 0.20 | 0.20 | 0.20 | 0.20 | 0.20 | 0.20 | 0.20 | 0.20 |
| Ammonium Polyacryloyldimethyl Taurate | 2.00 | 2.00 | 2.00 | 2.00 | 2.00 | 2.00 | 2.00 | 2.00 |
| Ethanol | 5.00 | 5.00 | 5.00 | 5.00 | 5.00 | 5.00 | 5.00 | 5.00 |
| Boron Nitride 1 | 0.75 | 0.75 | 0.75 | — | — | 0.75 | — | 0.75 |
| Pearlescent Pigment 1 (Titanium Dioxide (and) Mica (and) Tin Oxide) | 0.75 | 0.75 | — | 0.75 | 0.75 | — | 0.75 | 0.75 |
| Calcium Sodium Borosilicate | 1.00 | — | 1.00 | 1.00 | 1.00 | 1.00 | 1.00 | — |
| Silica | — | 1.00 | — | — | — | — | — | — |
| Titanium Dioxide | — | — | — | — | 0.75 | — | — | — |
| Boron Nitride 2 | — | — | — | — | — | — | 0.75 | — |
| Pearlescent Pigment 2 (Mica (and) Titanium Oxide) | — | — | — | — | — | 0.75 | — | — |

(Color of Reflection)
  Pearlescent Pigment 1: Blue
  Pearlescent Pigment 2: Blue
(Average Particle Size)
  Boron Nitride 1: about 2 μm
  Pearlescent Pigment 1: about 7 μm
  Boron Nitride 2: about 11 μm
  Pearlescent Pigment 2: about 20 μm
(Refractive Index)
  Boron Nitride 1: 1.74
  Boron Nitride 2: 1.74
  $TiO_2$: about 2.5
[Evaluations]
  0.2 g of each of the compositions according to Examples 1-2 and Comparative Examples 1-6 was applied onto half of the face of 6 panelists to evaluate the difference between the applied half of the face and the bare skin, in terms of the trace on skin after application, brightness, spot hiding, pore and relief hiding, and skin reflection, based on the following criteria.
Weak: barely noticeable
Medium: somewhat noticeable
Strong: noticeable
Very Strong: obvious
  The results are shown in Table 2.

It can be recognized from the comparisons of Examples 1-2 and Comparative Examples 1-6, shown in Tables 1 and 2, that a combination of the (a) plate type filler having a particle size of 10 μm or less and a refractive index of 2.0 or less, the (b) pearlescent pigment having a particle size of 15 μm or less and a colored reflection, and the (c) hollow or porous particle can decrease the visibility of skin color defects such as spots and/or microreliefs on skin such as pores and fine lines, providing skin with brightness, without providing skin with a glittering appearance and unnatural finish.

In particular, it can be recognized from the comparison of Example 1 and Comparative Example 1, that if the (b) pearlescent pigment is not used, it is difficult for the composition to decrease the visibility of skin color defects and/or microreliefs on skin, and to provide skin with sufficient brightness.

It can also be recognized from the comparison of Example 1 and Comparative Example 2 that, if the (a) plate type filler is not used, it is difficult for the composition to decrease the visibility of skin color defects and/or microreliefs on skin, and to provide skin with a sufficient brightness.

It can also recognized from the comparison of Example 1 and Comparative Example 3 that, the refractive index of the (a) plate type filler being 2.0 or less is important, because the

TABLE 2

|  | Ex. 1 | Ex. 2 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Traces on Skin after Application | Weak | Weak | Weak | Weak | Very Strong* | Strong** | Weak | Weak |
| Brightness | Strong | Strong | Weak | Weak | Very Strong | Medium | Medium | Medium |
| Spot Hiding | Strong | Strong | Weak | Weak | Strong | Medium | Medium | Medium |
| Pore and Relief Hiding | Strong | Strong | Medium | Medium | Strong | Medium | Medium | Medium |
| Skin Reflection | Medium | Weak | Medium | Medium | Weak | Strong | Strong | Medium |

*white traces were found,
**blue traces were found use of a particle having a refractive index of about 2.5 (TiO$_2$) in Comparative Example 3 provides too strong a brightness and unnatural finish.

It can also recognized from the comparison of Example 1 and Comparative Example 4 that, the particle size of the (b) pearlescent pigment being 15 μm or less is important, because the use of particle having a particle size of about 20 μm (Pearlescent Pigment 2) in Comparative Example 4 cannot decrease well the visibility of skin color defects and/or microreliefs on skin, cannot provide skin with sufficient brightness, and provides a glittering appearance and unnatural finish.

It can also recognized from the comparison of Example 1 and Comparative Example 5 that, the particle size of the (a) plate type filler being 10 μm or less is important, because the use of a particle having a particle size of about 11 μm (Boron Nitride 2) in Comparative Example 5 cannot decrease well the visibility of skin color defects and/or microreliefs on skin, cannot provide skin with a sufficient brightness, and provides a glittering appearance.

It can also recognized from the comparison of Example 1 and Comparative Example 6 that, if the (c) hollow or porous particle is not used, the composition cannot decrease well the visibility of skin color defects and/or microreliefs on skin, and cannot provide skin with sufficient brightness.

It can also recognized from the comparison of Examples 1 and 2 that, both of hollow and porous particles can be used with the ingredient "(c) hollow or porous particle".

Example 3

[Preparation]

The composition according to Example 3 (Ex. 3) was prepared by mixing the ingredients shown in Table 3. The numerical values for the amounts of the ingredients are all based on "% by weight" as active raw materials.

TABLE 3

|  | Ex. 3 |
| --- | --- |
| Water | qsp 100 |
| Phenoxyethanol | 0.7 |
| Glycerin | 5.0 |
| Butylene Glycol | 3.0 |
| Disodium EDTA | 0.1 |
| Chlorphenesin | 0.2 |
| Ammonium Polyacryloyldimethyl Taurate | 0.2 |
| Acrylates/C10-30 Alkyl Acrylate Crosspolymer | 0.4 |
| Xanthan Gum | 0.2 |
| Sodium Hyaluronate | 0.1 |
| Octyldodecanol | 1.5 |
| PPG-5 Ceteth-20 | 3.0 |
| Dimethicone (and) Dimethicone/Vinyl Dimethicone Crosspolymer | 6.0 |
| Dimethicone | 6.0 |
| Boron Nitride | 0.6 |
| Titanium Dioxide (and) Mica (and) Tin Oxide | 1.2 |
| Calcium Sodium Borosilicate | 1.0 |
| Fragrance | 0.1 |

The composition according to Example 3 was able to decrease the visibility of skin color defects such as spots, and also hide pores and fine lines while providing natural finish and a translucent aspect of the composition.

The invention claimed is:

1. A composition for a keratin substance, comprising:
   at least one filler having a particle size of 3 μm or less and having an aspect ratio of at least five, wherein the aspect ratio is computed as an average particle length divided by an average particle thickness;
   at least one pearlescent pigment comprising mica, a titanium oxide, and a tin oxide, and having a particle size of 15 μm or less; and
   at least one hollow or porous particle,
   wherein:
      the at least one filler comprises boron nitride and has a refractive index of 1.6 to 1.8, and
      the at least one pearlescent pigment has a colored reflection.

2. The composition according to claim 1, wherein:
   the at least pearlescent pigment has a particle size of 12 μm or less.

3. The composition according to claim 1, wherein the at least one filler has a particle size of 0.1 μm or more.

4. The composition according to claim 1, wherein the at least one filler has a refractive index of about 1.74.

5. The composition according to claim 1, wherein the at least one filler consists essentially of boron nitride.

6. The composition according to claim 1, wherein the amount of the at least one filler ranges from 0.001% to 10% by weight, relative to the total weight of the composition.

7. The composition according to claim 1, wherein the amount of the at least one filler ranges from 0.01% to 5% by weight, relative to the total weight of the composition.

8. The composition according to claim 1, wherein the at least one pearlescent pigment has a blue reflection.

9. The composition according to claim 1, wherein the at least one pearlescent pigment has a particle size of 1 μm or more.

10. The composition according to claim 1, wherein the at least one pearlescent pigment further comprises at least one metal oxide chosen from iron oxides and chromium oxides.

11. The composition according to claim 1, wherein the amount of the at least one pearlescent pigment ranges from 0.001% to 10% by weight, relative to the total weight of the composition.

12. The composition according to claim 1, wherein the amount of the at least one pearlescent pigment ranges from 0.01% to 5% by weight, relative to the total weight of the composition.

13. The composition according to claim 1, wherein the at least one hollow or porous particle has a particle size of 15 μm or less.

14. The composition according to claim 1, wherein the at least one hollow or porous particle has a particle size of 12 μm or less.

15. The composition according to claim 1, wherein the at least one hollow or porous particle comprises at least one inorganic material selected from the group consisting of mica, synthetic mica, talc, sericite, boron nitride, glass, calcium carbonate, barium sulfate, titanium oxide, hydroxyapatite, silica, silicate, calcium sodium borosilicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, or mixtures thereof.

16. The composition according to claim 1, wherein the amount of the at least one hollow or porous particle ranges from 0.001% to 10% by weight, relative to the total weight of the composition.

17. The composition according to claim 1, wherein the amount of the at least one hollow or porous particle ranges from 0.01% to 5% by weight, relative to the total weight of the composition.

18. A cosmetic process comprising:
applying to a keratin substance:
- at least one filler having a particle size of 3 µm or less and having an aspect ratio of at least five, wherein the aspect ratio is computed as an average particle length divided by an average particle thickness;
- at least one pearlescent pigment comprising mica, a titanium oxide, and a tin oxide, and having a particle size of 15 µm or less; and
- at least one hollow or porous particle, wherein:
- the at least one filler comprises boron nitride and has a refractive index of 1.6 to 1.8, and
- the at least one pearlescent pigment has a colored reflection, on the keratin substance, for sufficiently covering imperfections on the keratin substance, while providing the keratin substance with brightness.

\* \* \* \* \*